US012685875B2

(12) United States Patent
Quon et al.

(10) Patent No.: US 12,685,875 B2
(45) Date of Patent: Jul. 21, 2026

(54) METHOD AND DEVICE USING LIGHT ENERGY TO TREAT HERPES ZOSTER, HERPES SIMPLEX, AND OTHER VIRAL INFECTIONS WITH LOCALIZED SKIN OR MUCOSAL INFLAMMATION

(71) Applicants: Justin C Quon, San Marino, CA (US); David K Quon, San Marino, CA (US)

(72) Inventors: Justin C Quon, San Marino, CA (US); David K Quon, San Marino, CA (US)

( * ) Notice: Subject to any disclaimer, the term of this patent is extended or adjusted under 35 U.S.C. 154(b) by 288 days.

(21) Appl. No.: 18/239,417

(22) Filed: Aug. 29, 2023

(65) Prior Publication Data

US 2025/0073486 A1     Mar. 6, 2025

(51) Int. Cl.
*A61N 5/06* (2006.01)
*A61N 5/067* (2006.01)

(52) U.S. Cl.
CPC .... *A61N 5/0616* (2013.01); *A61N 2005/0626* (2013.01); *A61N 2005/0651* (2013.01); *A61N 2005/0654* (2013.01); *A61N 2005/066* (2013.01); *A61N 2005/0663* (2013.01); *A61N 5/067* (2021.08)

(58) Field of Classification Search
CPC ... A46B 15/0034; A46B 15/0036; A46B 7/04; A46B 9/04; A61B 5/0071; A61B 5/0088; A61N 5/0603; A61N 2005/0606; A61N 5/0616; A61N 5/067; A61N 2005/0626; A61N 2005/0651; A61N 2005/0654; A61N 2005/066; A61N 2005/0663; A61F 7/007; A61F 7/02; A61F 2007/0003; A61F 2007/0017; A61F 2007/0052; A61F 2007/0073; A61F 2007/0078; A61F 2007/0086; A61F 2007/0087; A61F 2007/0093; A61F 2007/0096; A61F 2007/0284
See application file for complete search history.

(56) References Cited

U.S. PATENT DOCUMENTS

| | | | | | |
|---|---|---|---|---|---|
| 5,500,009 | A | * | 3/1996 | Mendes | ............... A61N 5/0616 606/9 |
| 7,160,287 | B1 | * | 1/2007 | Siegel | ................... A61N 5/0616 606/3 |
| 2009/0005631 | A1 | * | 1/2009 | Simenhaus | ............... A61N 2/06 372/37 |
| 2024/0008745 | A1 | * | 1/2024 | König | .................. A61B 5/0088 |
| 2024/0261591 | A1 | * | 8/2024 | Miskin | ................. A61N 5/0624 |

* cited by examiner

*Primary Examiner* — Adam Z Minchella
(74) *Attorney, Agent, or Firm* — Ying-Ting Chen

(57) ABSTRACT

A light energy treatment method for target areas of skin or mucosa infected by herpes virus or other viral infections includes providing a plurality of light sources which generate light energy having a wavelength between 620 nm to 1500 nm; generating a series of light energy from the light sources in continuous wave mode or in pulsed mode with a pulse rate of 1 to 10000 Hz; applying the light energy in continuous wave mode or in pulsed mode to target areas of the skin or mucosa for 1 to 2000 seconds to achieve a power density between 20-500 mw/cm2; and stimulating cell mitochondria of the target areas of the skin or mucosa to increase cellular energy in the target areas of the skin or mucosa for cellular repair.

9 Claims, 4 Drawing Sheets

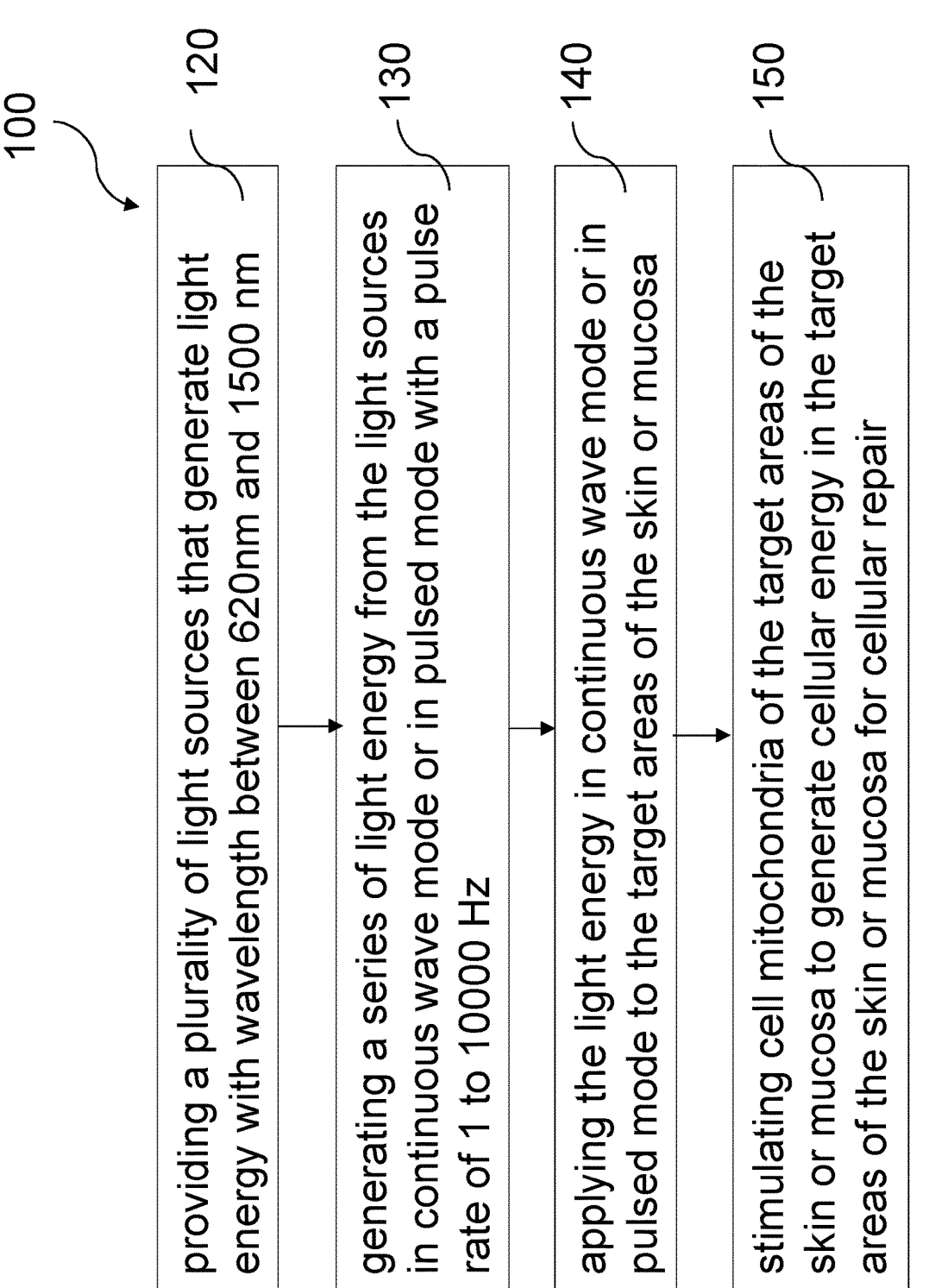

120 providing a plurality of light sources that generate light energy with wavelength between 620nm and 1500 nm 130 generating a series of light energy from the light sources in continuous wave mode or in pulsed mode with a pulse rate of 1 to 10000 Hz 140 applying the light energy in continuous wave mode or in pulsed mode to the target areas of the skin or mucosa 150 stimulating cell mitochondria of the target areas of the skin or mucosa to generate cellular energy in the target areas of the skin or mucosa for cellular repair

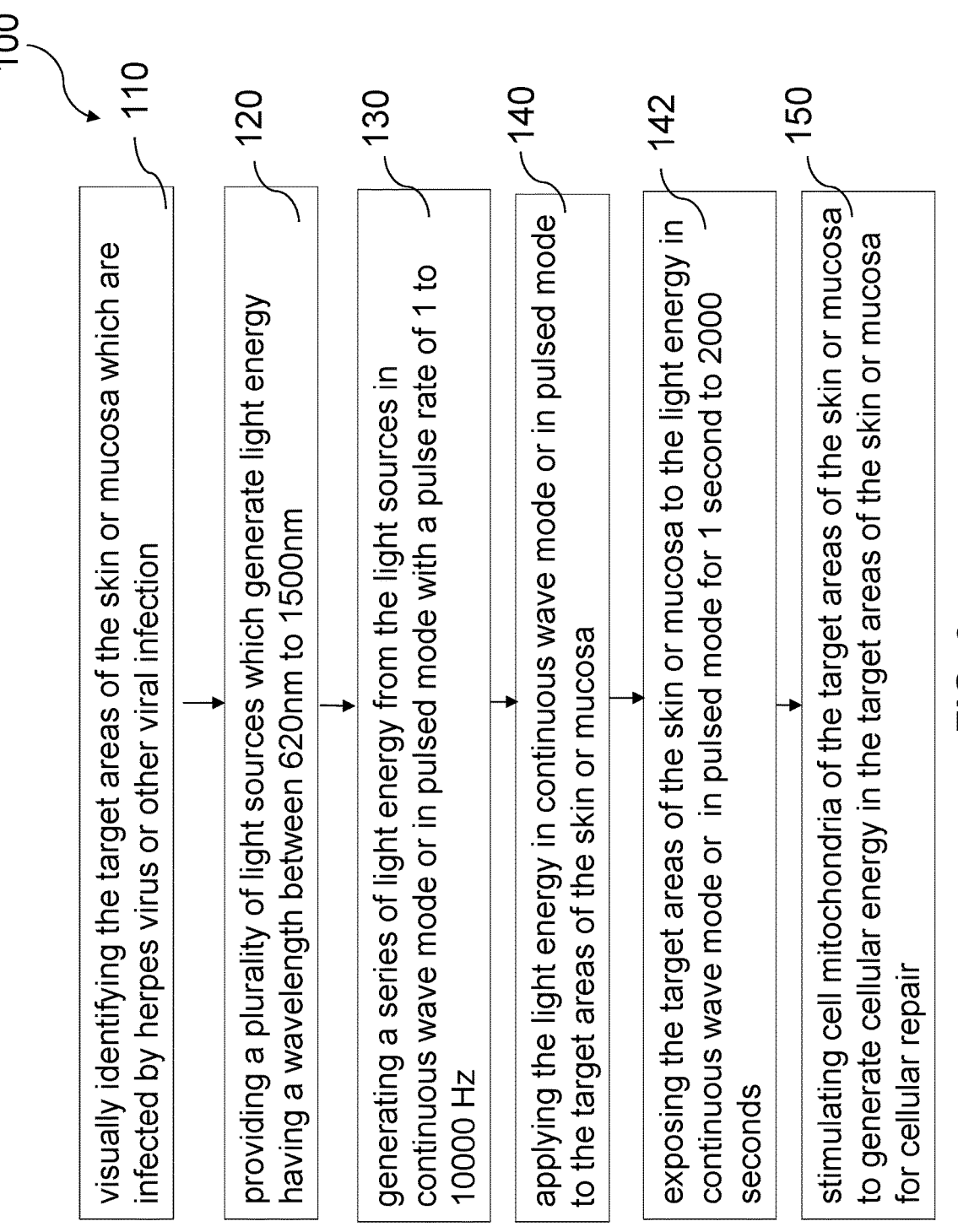

100

110 visually identifying the target areas of the skin or mucosa which are infected by herpes virus or other viral infection

120 providing a plurality of light sources which generate light energy having a wavelength between 620nm to 1500nm

130 generating a series of light energy from the light sources in continuous wave mode or in pulsed mode with a pulse rate of 1 to 10000 Hz

140 applying the light energy in continuous wave mode or in pulsed mode to the target areas of the skin or mucosa

142 exposing the target areas of the skin or mucosa to the light energy in continuous wave mode or in pulsed mode for 1 second to 2000 seconds

150 stimulating cell mitochondria of the target areas of the skin or mucosa to generate cellular energy in the target areas of the skin or mucosa for cellular repair

FIG. 3

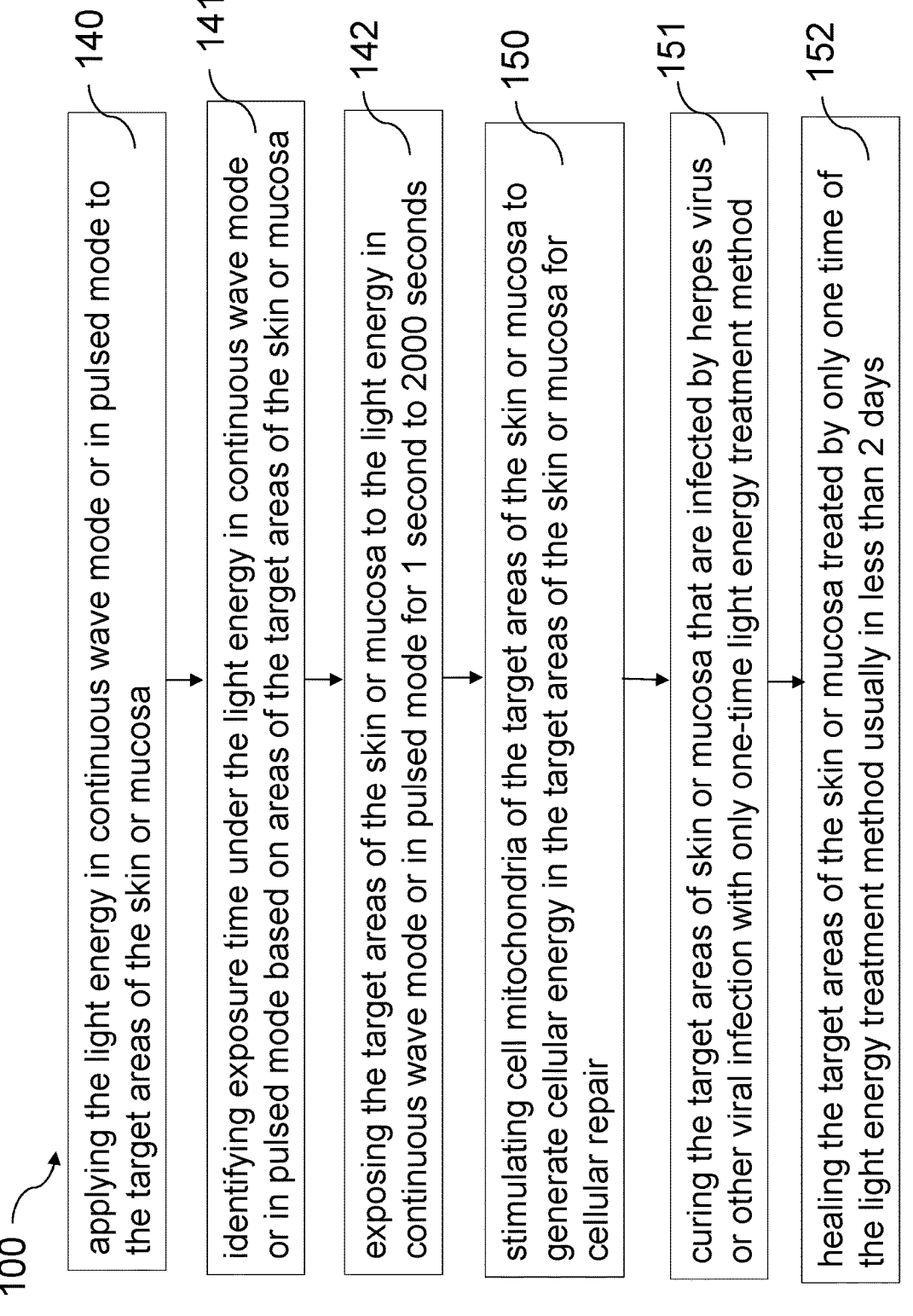

100

140 — applying the light energy in continuous wave mode or in pulsed mode to the target areas of the skin or mucosa 141 — identifying exposure time under the light energy in continuous wave mode or in pulsed mode based on areas of the target areas of the skin or mucosa 142 — exposing the target areas of the skin or mucosa to the light energy in continuous wave mode or in pulsed mode for 1 second to 2000 seconds 150 — stimulating cell mitochondria of the target areas of the skin or mucosa to generate cellular energy in the target areas of the skin or mucosa for cellular repair 151 — curing the target areas of skin or mucosa that are infected by herpes virus or other viral infection with only one-time light energy treatment method 152 — healing the target areas of the skin or mucosa treated by only one time of the light energy treatment method usually in less than 2 days

FIG. 4

METHOD AND DEVICE USING LIGHT ENERGY TO TREAT HERPES ZOSTER, HERPES SIMPLEX, AND OTHER VIRAL INFECTIONS WITH LOCALIZED SKIN OR MUCOSAL INFLAMMATION

FIELD OF THE DISCLOSURE

The present disclosure relates to a treatment device and method for herpes zoster, herpes simplex, and other viral infections with localized skin or mucosal inflammation using coherent or noncoherent light with wavelengths between 620 nm and 1500 nm, fluence level from 0.1 to 30 Joules per centimeter squared, exposure time from 1 second to 2000 seconds, and power density between 20-500 mw/cm2 to achieve efficacious treatment with minimal adverse effects.

BACKGROUND OF THE DISCLOSURE

Both herpes zoster and herpes simplex are due to infections by viruses in the Herpes family. Herpes zoster results from viral reactivation in a person previously infected with the varicella-zoster virus, a member of the Herpes family that causes chickenpox. After chickenpox, the virus becomes dormant in the dorsal root ganglion, often for decades. The virus may reactivate as host immunity wanes, usually presenting with initial pain and itching, followed by painful blisters days later, which crust in one to three weeks. This reactivation results in the clinical condition known as herpes zoster. The location of the reactivation is usually limited to one or two adjacent dermatomes on one side of the body. Usual locations are across the back, chest, and abdomen on one side of the body, one leg from the proximal region to the lower region, and areas involving the forehead and the upper face on one side of the body. Herpes zoster is a common infection. According to the Center for Disease Control (CDC), over 99% of the population in the US born before 1980 had chickenpox, and in this reservoir, an estimated one million cases of reactivation occur yearly. Reactivation usually happens only once but may be recurrent. Medical treatment for herpes zoster usually involves using one of three antiviral medications (acyclovir, valacyclovir, and famciclovir). Antiviral medications are used to shorten the duration and lessen the disease severity, and common side effects include headache, dizziness, fatigue, and gastrointestinal symptoms. Herpes zoster not only causes mucocutaneous inflammation but also causes nerve damage. Despite treatment, the CDC estimates that 10 to 18% of patients with herpes zoster will develop a clinical condition known as post-herpetic neuralgia (PHN) with severe and often debilitating pain in the area of reactivation that may last up to years. The risk of PHN is proportional to the duration of inflammation and blistering. There is currently a vaccine known as Shingrix that offers approximately 90% protection against herpes zoster and PHN among people at age 70, and the effectiveness should last at least seven years. However, the effectiveness wanes with advancing age and weakened immunity, which are both conditions inductive to herpes zoster, to as low as 60%. Effectiveness also wanes with time after administration. Side effects of the Shingrix vaccine ranges from common findings of muscle pain, fatigue, headache, and gastrointestinal symptoms, to a rare but potentially fatal neurological condition known as Guillain-Barre syndrome. In 2019, the CDC estimated that 26.1% of adults over age 50 had ever received at least one dose of the Shingrix vaccine, which is usually administered in two doses within six months. Herpes simplex also belongs to the Herpes family. It includes herpes simplex type 1 (HSV-1) and herpes simplex type 2 (HSV-2). HSV-1 is usually associated with mouth and lip sores and blisters. HSV-2 is usually known as genital herpes and causes sores and blisters in the genital and anal regions. Depending on contact and transmission source, both HSV-1 and HSV-2 are capable of causing infection in the mouth and genital regions. An estimated 50 to 80% of American adults have oral herpes simplex. It is estimated that over 570,000 new cases of genital herpes occur each year. The prevalence of genital herpes among 14 to 49 year old Americans is estimated to be 11.9% by the CDC. Both HSV-1 and HSV-2 can remain dormant and asymptomatic or can reactivate to cause blisters and ulcers. Frequent recurrence is common for both HSV-1 and HSV-2. Besides local soothing measures, medical treatment usually involves the use of one of the three antiviral medications for herpes (acyclovir, valacyclovir, and famciclovir) with similar adverse effects as they are used in the treatment of herpes zoster. Because of morbidity, many people take long term suppressive therapy for genital herpes. The duration of suppressive therapy usually lasts for decades. There currently is no vaccine for herpes simplex.

The most common presentation of herpes zoster and herpes simplex share the following characteristics: significant morbidity, localized skin and or mucosal lesion with inflammation due to viral infection, and increased risk in patients with decreased immunity.

The mainstay of the current treatment of herpes zoster and herpes simplex is the use of antiviral medications, which are intended to stop viral replication but do not address the issue of immunity and inflammation. Antiviral medications usually have limited efficacy and only result in a modest reduction of morbidity. These medications are usually safe but have side effects like any other medications, and the cost of care can be substantial.

There exists a need to treat herpes zoster, herpes simplex, and other viral infections with localized skin or mucosal lesions and inflammation with a safe, inexpensive, painless, effective, and time-saving method that may also boost immunity and decrease inflammation.

All referenced patents, applications and literature are incorporated herein by reference in their entirety. Furthermore, where a definition or use of a term in a reference, which is incorporated by reference herein, is inconsistent or contrary to the definition of that term provided herein, the definition of that term provided herein applies and the definition of that term in the reference does not apply. The disclosed embodiments seek to satisfy the above-mentioned needs. Although the present embodiments may obviate one or more of the above-mentioned desires, it should be understood that some aspects of the embodiments might not necessarily obviate them.

BRIEF SUMMARY OF THE DISCLOSURE

In a general implementation, a treatment method using light energy for localized skin or mucosal lesions and inflammation caused by herpes or other viral infections comprises steps of: providing a plurality of light sources which generate light energy having a wavelength between 620 nm to 1500 nm and a fluence level from 0.1 to 30 Joules per centimeter squared; generating a series of light energy in continuous wave or pulsed mode with a pulse rate of 1 to 10000 Hz; applying the light energy to target areas of the skin or mucosa; stimulating cell mitochondria to produce more cellular energy in the form of adenosine triphosphate

US 12,685,875 B2

3

(ATP) to fight the infection. The target areas of the skin or mucosa are the areas infected by herpes virus or other viral infections.

In another aspect combinable with the general implementation, the wavelength selected ranges from 620 nm to 1500 nm. Most commonly, the wavelengths selected are 630 nm, 660 nm, 680 nm, 810 nm, 980 nm, 1060 nm, 1300 nm, or a combination thereof.

Among the many possible implementations of the light treatment method for target areas of skin or mucosal membrane infected by herpes or other viral infections, the cellular energy is adenosine triphosphate (ATP).

Furthermore, it is contemplated that the light energy has a fluence level between 0.1 and 30 Joules per centimeter squared, which is sufficient to stimulate cell mitochondria to generate cellular energy in the target areas of the skin or mucosa infected by herpes or other viruses without burning the skin or the mucosa.

In the alternative, the series of light energy in pulsed mode has a peak power of up to and including 100 W.

It is still further contemplated that the light treatment method for target areas of skin or mucosa infected by herpes virus or other viral infections comprises steps of identifying the target areas of skin or mucosa infected by herpes virus or other viral infection.

In one embodiment, the light treatment method for target areas of skin or mucosa infected by herpes virus or other viral infections comprises steps of identifying exposure time under the light energy based on target areas of the skin or mucosa.

Another aspect of the embodiment is directed to the light treatment method for target areas of skin or mucosa infected by herpes virus or other viral infections, wherein the method further comprises a step of: exposing the target areas of the skin or mucosa to the light energy from 1 second to 2000 seconds to achieve power density between 20-500 mw/cm2.

In another aspect combinable with the general implementation, the light energy treatment method for target areas of skin or mucosa infected by herpes virus or other viral infections further comprises a step of: treating the target areas of skin or mucosa infected by herpes infection or other viral infection with light energy treatment method.

In another aspect combinable with the general implementation, the light energy treatment method for target areas of skin or mucosa infected by herpes or other viral infections comprises the step of selecting the light source from a group consisting of a laser, an incandescent lamp with appropriate filters, IPL lamp with appropriate filters, a laser diode, LED, or a combination of two or more of these sources.

In another aspect combinable with the general implementation, the light energy treatment method for target areas of skin or mucosa infected by herpes or viral infections, wherein the target areas of the skin or mucosa comprise lips of the mouth, skin, or mucosa of genital or anal regions, or any other body areas.

In another aspect combinable with the general implementation, the light energy treatment method for target areas of skin or mucosa infected by herpes virus or other viral infections may further comprise a step of reducing or reversing the inflammation in the actively infected areas of the skin or mucosa treated by the light energy treatment method no more than two days after the start of the light energy treatment method.

While this specification contains many specific implementation details, these should not be construed as limitations on the scope of any inventions or of what may be claimed, but rather as descriptions of features specific to particular implementations of particular inventions. Certain features that are described in this specification in the context of separate implementations can also be implemented in combination in a single implementation. Conversely, various features that are described in the context of a single implementation can also be implemented in multiple implementations separately or in any suitable subcombination. Moreover, although features may be described above and below as acting in certain combinations and even initially claimed as such, one or more features from a claimed combination can in some cases be excised from the combination, and the claimed combination may be directed to a subcombination or variation of a subcombination.

A number of implementations have been described. Nevertheless, it will be understood that various modifications may be made without departing from the spirit and scope of the disclosure. For example, example operations, methods, or processes described herein may include more steps or fewer steps than those described. Further, the steps in such example operations, methods, or processes may be performed in different successions than that described or illustrated in the figures. Accordingly, other implementations are within the scope of the following claims.

The details of one or more implementations of the subject matter described in this disclosure are set forth in the accompanying drawings and the description below. Other features, aspects, and advantages of the subject matter will become apparent from the description, the drawings, and the claims.

BRIEF DESCRIPTION OF THE DRAWINGS

It should be noted that the drawing figures may be in simplified form and might not be too precise scale. In reference to the disclosure herein, for purposes of convenience and clarity only, directional terms such as top, bottom, left, right, up, down, over, above, below, beneath, rear, front, distal, and proximal are used with respect to the accompanying drawings. Such directional terms should not be construed to limit the scope of the embodiment in any manner.

FIG. 1 illustrates a light energy treatment method for target areas of skin or mucosa infected by herpes virus or other viral infections according to an aspect of the embodiments.

FIG. 3 illustrates the light energy treatment method for target areas of skin or mucosa infected by herpes virus or other viral infections according to an aspect of the embodiments.

FIG. 4 illustrates the light energy treatment method for target areas of skin or mucosa infected by herpes virus or other viral infections according to an aspect of the embodiments.

DETAILED DESCRIPTION OF THE EMBODIMENTS

Figure 2:
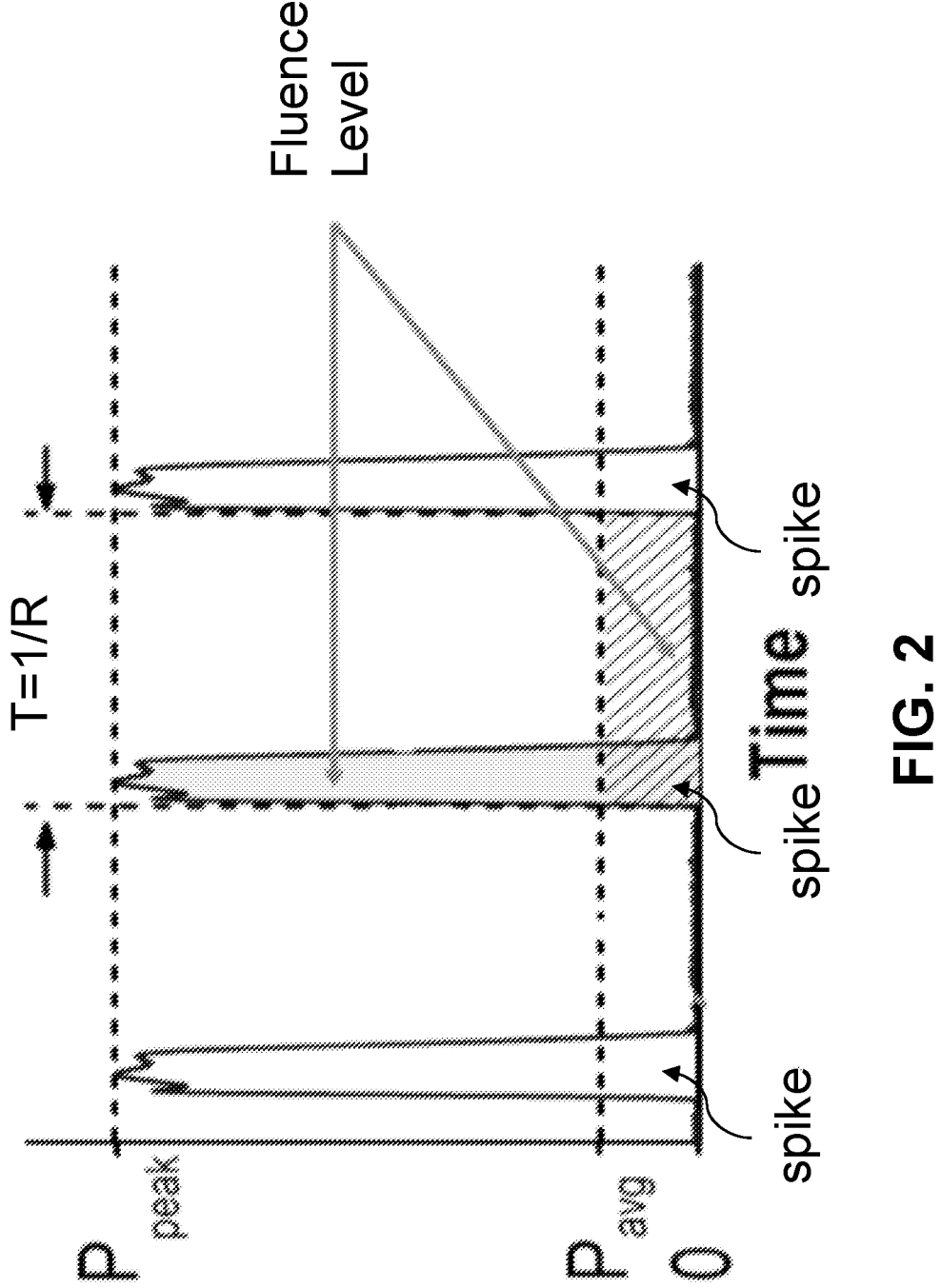
FIG. 2 illustrates a series of light energy in continuous wave mode or in a pulsed mode according to an aspect of the embodiments.

The different aspects of the various embodiments can now be better understood by turning to the following detailed description of the embodiments, which are presented as illustrated examples of the embodiments defined in the claims. It is expressly understood that the embodiments as defined by the claims may be broader than the illustrated embodiments described below.

The term "a" or "an" entity refers to one or more of that entity. As such, the terms "a" (or "an"), "one or more" and "at least one" can be used interchangeably herein. It is also to be noted that the terms "comprising," "including," and "having" can be used interchangeably.

It shall be understood that the term "means," as used herein, shall be given its broadest possible interpretation in accordance with 35 U.S.C., Section 112(f). Accordingly, a claim incorporating the term "means" shall cover all structures, materials, or acts set forth herein, and all of the equivalents thereof. Further, the structures, materials or acts and the equivalents thereof shall include all those described in the summary of the invention, brief description of the drawings, detailed description, abstract, and claims themselves.

Unless defined otherwise, all technical and position terms used herein have the same meaning as commonly understood by one of ordinary skill in the art to which the invention pertains. Although many methods and materials similar, modified, or equivalent to those described herein can be used in the practice of the present invention without undue experimentation, the preferred materials and methods are described herein. In describing and claiming the present invention, the following terminology will be used in accordance with the definitions set out below.

FIG. 1 generally depicts a light energy treatment method for target areas of skin or mucosa infected by herpes virus or other viral infections (100) according to an aspect of the embodiments.

Referring to FIG. 1, in some embodiments, the light energy treatment method (100) may comprise:

providing a plurality of light sources which generate light energy having a wavelength between 620 nm to 1500 nm (120);

generating a series of light energy from the light sources in a continuous wave mode or in a pulsed mode with a pulse rate of 1 to 10000 Hz (130);

applying the light energy in continuous wave mode or pulsed mode to the target areas of the skin or mucosa (140);

stimulating cell mitochondria of the target areas of the skin or mucosa to generate cellular energy in the target areas of the skin or mucosa for cellular repair (150).

In still some embodiments, the wavelength of the light energy may be selected from a group consisting of 630 nm, 660 nm, 810 nm, 980 nm, 1060 nm, 1300 nm, or a combination thereof, and in such a manner, the light energy may sufficiently stimulate the cell mitochondria to produce more cellular energy but not cause any significant harm to the target areas of the skin or mucosa. It should be noted that the light energy used in this invention mainly functions on the cellular levels.

In still some embodiments, the cellular energy may be adenosine triphosphate (ATP), wherein the adenosine triphosphate (ATP) may accelerate the healing process of target areas of the skin or mucosa infected by herpes virus or other viral infections.

FIG. 2 generally depicts the series of light energy in the continuous wave mode or in the pulsed mode according to an aspect of the embodiments.

Referring to FIG. 2, in still some embodiments, the series of light energy in pulsed mode may deliver light energy in a series of energy spikes, wherein each spike comprises a peak power to deliver a significantly higher level of energy. It should be noted that these series of energy spikes act to "stimulate" and cause more energy to be released from the mitochondria. Therefore, the pulsed mode is better for cellular defense, compared to the continuous mode.

In some embodiments, the series of light energy may have the pulse rate (R) of 1 to 10000 Hz and, more preferably, a pulse rate (R) between 100 to 1000 Hz, wherein the pulse rate (R) is the frequency with which pulses are emitted and is equal to the reciprocal of the period. The period (T) is the amount of time between the start of one pulse and the start of the next.

In some embodiments, the series of light energy may have a fluence level between 0.1 and 30 Joules per centimeter squared ($J/cm^2$) which is sufficient to stimulate cell mitochondria of the target areas of the skin or mucosa to generate cellular energy in the target areas of the skin or mucosa without burning the target areas of the skin or mucosa, wherein a measure of one pulse's total emission is the only light emitted by the light energy over the entire period. The pulse energy (the fluence level) equals the shaded area in FIG. 2, which is equivalent to the area covered by diagonal hash marks.

In some embodiments, the series of light energy may have a peak power (Ppeak) of up to 100 W, and preferably, the series of light energy may have an energy power ranging from 1 to 100 W.

In some embodiments, the target areas of the skin or mucosa comprise the lips of the mouth, skin, and mucosa of the genital or the anal areas or any body area.

It should be understood that the above-described target areas of the skin or mucosa is exemplary, and any other target areas of the skin or mucosa can be adopted in various embodiments of this disclosure.

FIG. 3 generally depicts the light energy treatment method for target areas of skin or mucosa infected by herpes virus or viral infections according to an aspect of the embodiments.

Referring to FIG. 3, the light energy treatment method (100) may further comprise steps of:

visually identifying the target areas of skin or mucosa which are areas infected by herpes virus or other viral infection (110).

providing a plurality of light sources which generate light energy having a wavelength between 620 nm to 1500 nm (120);

generating a series of light energy from the light sources in continuous wave mode or in pulsed mode with a pulse rate of 1 to 10000 Hz (130);

applying the light energy in continuous wave mode or in pulsed mode to the target areas of the skin or mucosa (140) for 1 to 2000 seconds to achieve a power density between 20 and 500 mw/cm2; and stimulating cell mitochondria of the target areas of the skin or mucosa to generate cellular energy in the target areas of the skin or mucosa for cellular repair (150).

In some embodiments, the herpes simplex infections may usually show as herpes sores appearing as one or more blisters or ulcers on or around the target areas of the skin or mucosa (usually the genitals, rectum, or mouth).

In some embodiments, the frequency of the emitted pulses of light is equal to the reciprocal of the period.

FIG. 4 generally depicts the light energy treatment method for target areas of skin or mucosa infected by herpes virus or viral infections according to an aspect of the embodiments.

It should be noted that, in still some embodiments, the light energy treatment method (100) may further comprise a step of:

identifying exposure time under the light energy based on areas of the target spots of the skin or mucosa (141).

In some embodiments, the light energy treatment method may further comprise a step of:

exposing the target areas of the skin or mucosa to the light energy for 1 second to 2000 seconds (142) to achieve a power density between 20 and 500 mw/cm2.

In some embodiments, the light energy treatment method may further comprise a step of:

curing the target areas of skin or mucosa infected by herpes virus or other viral infections with only one time treatment using the light energy treatment method (151).

In some embodiments, the light energy treatment method for target areas of skin or mucosa infected by herpes or viral infections may comprise steps of:

visually identifying the target areas of skin or mucosa which are infected by herpes virus or viral infection (110).

providing a plurality of light sources which generate light energy having a wavelength between 620 nm to 1500 nm (120);

generating a series of light energy from the light sources in continuous wave mode or in pulsed mode with a pulse rate of 1 to 10000 Hz (130);

applying the light energy in continuous mode or in pulsed mode to the target areas of the skin or mucosa (140);

identifying exposure time under the light energy based on locations and sizes of the target areas of the skin or mucosa (141);

exposing the target areas of the skin or mucosa to the light energy for 1 second to 2000 seconds to achieve a power density between 20 and 500 mw/cm2 (142);

stimulating cell mitochondria of the target areas of the skin or mucosa to generate cellular energy in the target areas of the skin or mucosa for cellular repair (150);

curing the target areas of skin or mucosa infected by herpes virus or viral infection with only one-time light energy treatment method in this invention (151).

In some embodiments, the light energy treatment method may further comprise a step of: reducing and reversing the inflammation no more than two days after light energy treatment in the target areas of the skin or mucosa treated with only one time of the light energy treatment method.

According to all of the embodiments mentioned above, the light energy in continuous wave mode or in pulsed mode may function at the cellular levels of the target areas of the skin or mucosa.

It should be noted, in still some embodiments, after only one time treatment using the light energy treatment method in this invention (100), more than 99% of herpes zoster or herpes simplex infections are cured. The traditional medical treatments may take 10 days or more to show effective results, and the present light energy treatment method is a non-invasive treatment method and usually requires only one time treatment from 30 seconds to 30 minutes on targeted areas of the skin or mucosa anywhere on the body. The duration of the one-time treatment depends on the size of the lesions and the sizes of light beams from the light energy source. The present light energy treatment provides a quick recovery period and greatly reduces post-herpetic neuralgia (PNH). With these embodiments of the light energy treatment method mentioned above, fewer than 1% of the patients have reported PHN pain after herpes zoster is cured.

It should be noted that, in some embodiments, the series of light energy in pulsed mode delivers the higher peak energy. Between the light energy in both the continuous wave mode and the pulsed mode, the light energy in the pulsed mode works much better than the continuous wave mode, based on many patients having the above clinical light energy treatment method (100).

According to the embodiments mentioned above, the light source is selected from a group consisting of a laser, an incandescent lamp with appropriate filters to allow passage of light with wavelengths between 620 nm and 1500 nm, IPL lamp with similar appropriate filters, a laser diode, a LED, or a combination of two or more of these sources.

It should be understood that the above-described light sources are exemplary and many other light sources can be adopted in various embodiments of this disclosure.

According to all of the embodiments mentioned above, lasers with wavelengths in the red and near-infrared wavelengths may be utilized to stimulate the mitochondria to produce cellular energy (i.e., ATP) for cellular repair and defense. These wavelengths when used according to the present invention do not "burn" or harm the skin or mucosa, and their biological actions are mainly on the cellular level.

The present invention shows that the light energy in pulsed mode works much better than the continuous wave mode in hundreds of treated cases. Typically, using light energy in pulsed mode, only one treatment to treat these lesions (herpes zoster, herpes simplex, or other viral infections) is needed to see excellent results overnight.

Example of the Light Energy Treatment Method

The patient is diagnosed by the physician as having herpes zoster or herpes simplex infection with typical localized skin or mucosal lesions. Target areas of skin or mucosa that are infected are identified. The light energy in pulsed mode is applied to target areas of skin or mucosa. The specification of the light energy is: a wavelength between 620 nm and 1500 nm, a pulse rate of 1 to 10000 Hz, a Peak power (Ppeak) of 100 W, and an exposure time of about 2 to 3 minutes.

Results

After only one time treatment using the light energy treatment method of the present invention in a typical case, the active herpes zoster blisters become dry and are no longer infective within two days. The typical response of the light energy treatment includes reduced pain, swelling, and erythema with crust formation overnight. The light energy treatment of the present invention is effective, painless, inexpensive, and apparently without any side effects.

Many alterations and modifications may be made by those having ordinary skill in the art without departing from the spirit and scope of the disclosed embodiments. Therefore, it must be understood that the illustrated embodiments have been set forth only for the purposes of example and that it should not be taken as limiting the embodiments as defined by the following claims. For example, notwithstanding the fact that the elements of a claim are set forth below in a certain combination, it must be expressly understood that the embodiment includes other combinations of fewer, more, or different elements, which are disclosed herein even when not initially claimed in such combinations.

Thus, specific embodiments and applications of the light energy treatment method for target spots of skin or mucosa infected by herpes virus or other viral infections have been disclosed. It should be apparent, however, to those skilled in the art that many more modifications besides those already described are possible without departing from the disclosed concepts herein. Therefore, the disclosed embodiments are not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Insubstantial changes from the claimed subject matter as viewed by a person with ordinary skill in the art, now known or later devised, are expressly contemplated as equivalent within the scope of the claims. Therefore, obvious substitutions now or later known to one with ordinary skill in the art are defined to be within the scope of the defined elements. The claims are thus to be understood to include what is specifically illustrated and described above, what is conceptually equivalent, what can be substituted and also what essentially incorporates the essential idea of the embodiments. In addition, where the specification and claims refer to at least one of something selected from the group consisting of A, B, C . . . and N, the text should be interpreted as requiring at least one element from the group which includes N, not A plus N, or B plus N, etc.

The words used in this specification to describe the various embodiments are to be understood not only in the sense of their commonly defined meanings but to include by special definition in this specification structure, material or acts beyond the scope of the commonly defined meanings. Thus, if an element can be understood in the context of this specification as including more than one meaning, then its use in a claim must be understood as being generic to all possible meanings supported by the specification and by the word itself.

The definitions of the words or elements of the following claims therefore include not only the combination of elements which are literally set forth but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

What is claimed is:

1. A light energy treatment method for target areas of skin or mucosa infected by herpes virus or other viral infections, comprising:

providing a plurality of light sources which generate light energy having a wavelength consisting of 810 nm and 1302 nm;

generating a series of light energy from the light sources in pulsed mode with a pulse rate of 300 to 10000 Hz;

applying the light energy in pulsed mode only one time to the target areas of the skin or mucosa, with the target areas of skin or mucosa being the areas infected by the herpes virus or other viral infections;

exposing the target areas of the skin or mucosa under the light energy in pulsed mode for 1 second to 2000 seconds the only one time to achieve a power density between 20 and 500 mw/cm$^2$;

stimulating cell mitochondria of the target areas of the skin or mucosa to generate cellular energy in the target areas of the skin or mucosa for cellular repair; and curing the target areas of the skin infected by herpes including herpes zoster and/or herpes simplex, and other viral infections with localized mucocutaneous inflammation in no more than two days by using only a one-time low-level light energy treatment method; wherein the light source is a LED.

2. The method of claim 1, wherein the cellular energy is adenosine triphosphate.

3. The method of claim 1, wherein the light energy has a fluence level between 0.1 and 30 Joules per centimeter squared, which is sufficient to stimulate cell mitochondria of the target areas of the skin or mucosa to generate cellular energy in the target areas of the skin without burning the target areas of the skin or mucosa.

4. The method of claim 1, wherein the series of light energy in pulsed mode has a peak power of up to 100 W.

5. The method of claim 1, further comprising a step of: visually identifying the target areas of the skin or mucosa which are skin or mucosal surfaces infected by herpes virus or other viral infection.

6. The method of claim 1, further comprising a step of: identifying exposure time under the light energy based on locations and sizes of the target areas of the skin or mucosa.

7. The method of claim 1, further comprising a step of: curing the target areas of the skin infected by herpes including herpes zoster and/or herpes simplex, and other viral infections with localized mucocutaneous inflammation in no more than two days by using only a one-time low-level light energy treatment method.

8. The method of claim 1, wherein the target areas of the skin comprise lips of the mouth, skin, or mucosa in the genital and anal regions.

9. The method of claim 1, further comprising a step of: promptly healing in the target areas of the skin or mucosa treated by only one time of the light energy treatment method no more than two days after treatment.

* * * * *